United States Patent [19]

Rimland

[11] Patent Number: 4,755,140

[45] Date of Patent: Jul. 5, 1988

[54] ELECTRONIC PERSONNEL TEST DEVICE

[76] Inventor: Bernard Rimland, 4758 Edgeware Rd., San Diego, Calif. 92116

[21] Appl. No.: 835,861

[22] Filed: Feb. 10, 1986

[51] Int. Cl.$^4$ .............................................. G09B 7/04
[52] U.S. Cl. ................................ 434/236; 273/1 GE; 273/1 G; 273/1 E
[58] Field of Search ............ 434/236; 273/1 GE, 1 G, 273/1 E

[56] References Cited

U.S. PATENT DOCUMENTS

| 3,024,020 | 3/1962 | Alton | 273/1 GE |
| 3,641,686 | 2/1972 | Krass | 434/236 |
| 4,464,121 | 8/1984 | Perelli | 434/236 |

FOREIGN PATENT DOCUMENTS 578339  8/1976  Switzerland ................ 273/1 GE

Primary Examiner—Leo P. Picard
Attorney, Agent, or Firm—Robert F. Beers; Ervin F. Johnston; Thomas Glenn Keough

[57] ABSTRACT

A device resembling a hand calculator provides an indicator of a subject's reaction time. An array of pushbutton keys has programmably varied numerals which do not correspond to an orderly presentation. A display on the device instructs that a particular sequence of numbers be touch-indicated by the subject within a certain period of time. The touched sequence and time elapsed provides an indication of the subject's reaction time which could be influenced by fatigue, ill health and drug, including alcohol, use so that the subject's effectiveness for a particular duty can be evaluated.

2 Claims, 6 Drawing Sheets

ELECTRONIC PERSONNEL TEST DEVICE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Many jobs have hazardous conditions which require that workmen or others closely involved be alert and have quick reaction times. In addition to jobs in which there are exposures to hazardous life-threatening conditions, other jobs require the making of intelligent, quick decisions with clear, unimpaired minds.

One application where clarity of mind is acutely felt is in the evaluation of the effectiveness, and hence, security, at large installations patrolled by security forces. A guard's awareness and reaction time oftentimes are the determining factors in the safety of others and security of an installation. Long-distance truck drivers and nuclear reactor operators are other examples. Reaction and alertness are linked definitely to changes in a psychological state and chemical activity in the brain. Psychological state and chemical activity can be the product of fatigue, illness, medication, alcohol or illicit drug use.

A number of elaborate testing devices and written questionnaires have evolved that may give supervisory personnel, police or inspectors an indication of an individual's mental state and alertness, however, generally they tend to be rather time-consuming and cumbersome and do not lend themselves to an on-the-job, expedient testing. There exists no device by which an individual can be tested quickly in a manner which will not require the use of cumbersome and complicated devices or by unduly time consuming, yet will provide a reliable check of the individual's reaction time and alertness.

Thus there is a continuing need in the state-of-the-art for a portable and accurate testing device for an individual's mental condition and reaction time.

SUMMARY OF THE INVENTION

The present invention is directed to providing a quick and a reliable means for monitoring the alertness and reaction time of a subject. A hand calculator-like device has randomly arranged numerical designations next to push-button keys and a computer display which shows a scrambled sequence of numbers to be punched into the device by the subject. The time it takes and the errors made are recorded and compared with the times and error rates that the same subject has made during previous tests under controlled conditions, or with times and error rates made by normal subjects not impaired by fatigue, alcohol or drugs. Thus, an on-the-spot evaluation can be made and any deviation can be noted and appropriate action initiated.

A prime object is to provide for an expedient alertness and reaction time indicator.

Still another object is to provide for the hand-held reaction time indicator that relies on an individual's selective responses to randomly presented sequences of numbers.

Still another object is to provide a hand-held reaction time indicator capable of being restructured to compensate for an individual's memorizing a particular number sequence of keyboard numerals.

Still another object is to provide for a reprogrammable reaction time indicator suitable for comparison with a particular individual's own history of reaction times to show deviations from normalized reaction times, or with standards for normal subjects unimpaired by fatigue, alcohol or drugs.

Yet another object is to provide a testing device and method that can be administered by unspecialized personnel without elaborate associated equipments.

Other objects, advantages and novel features of the invention will become apparent from the following detailed description and claims of the invention when considered in conjunction with the accompanying drawings.

DESCRIPTION OF THE PREFERRED EMBODIMENT

Figure 1:
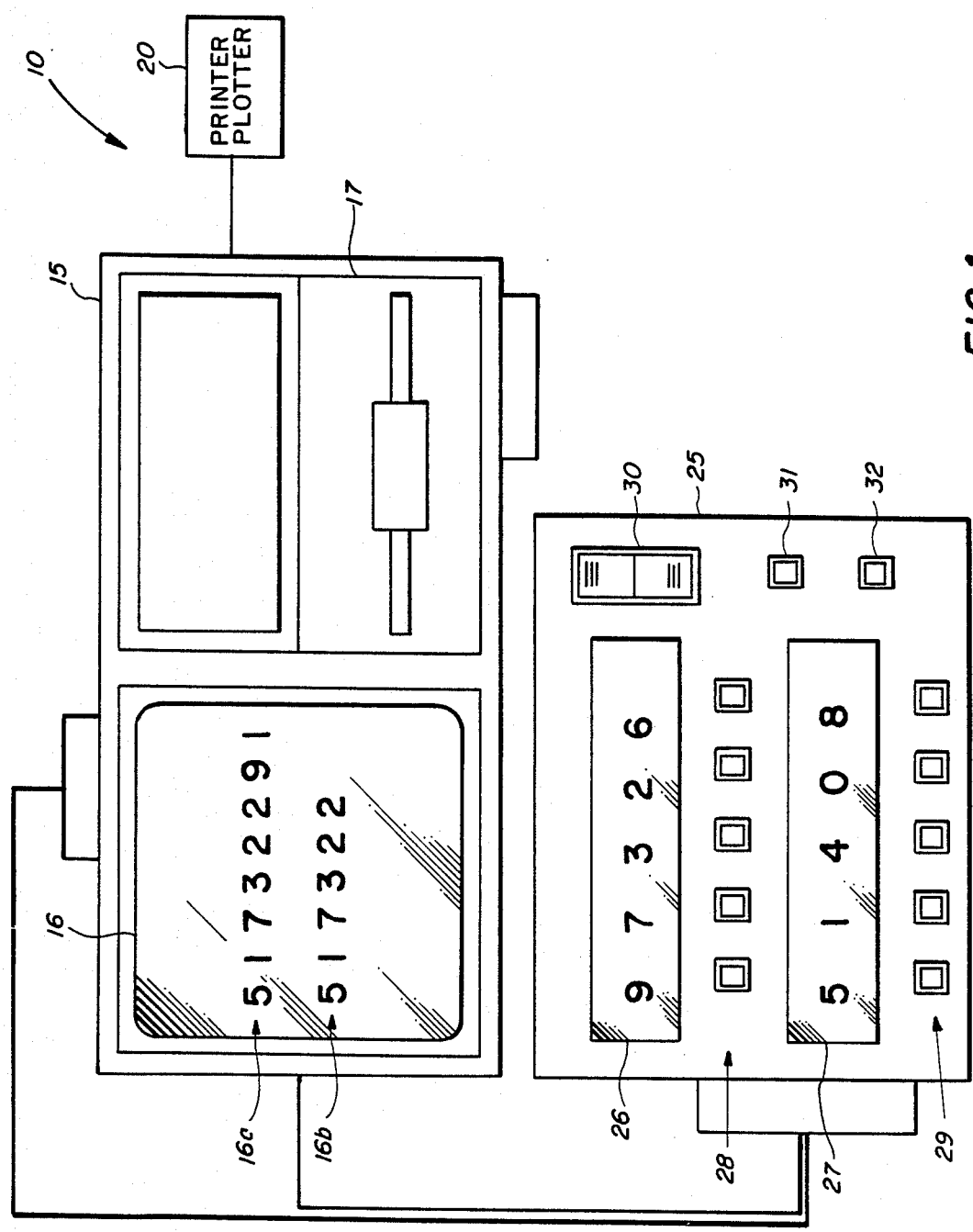
FIG. 1 is an isometric depiction of a typical reaction time indicator device for displaying a randomized numerical presentation with a scrambled array of push-button keys.

Referring now to the drawings and in particular to FIG. 1 thereof, an electronic personnel test device 10 is compactly packaged to allow its transport and use at a work site. Since in this configuration it is a complete unit, it also can be used at a permanent test facility to determine mental condition and responsiveness.

This embodiment has a microcomputer section 15 with its associated plotter 20 and a hand-held push-button keyboard 25. Cables are shown to link the three components together although a short range radio capability can be included with respect to the computer-keyboard interface. The radio link can be quite similar to the system associated with remotely operated telephones, for example.

A microcomputer selected for a typical realization of this inventive concept was a commercially available unit marked under the trademark Commodore SX 64. This unit was chosen since it has the capabilities to perform the tasks elaborated on below with little or no modification. The software to perform the testing sequences is well within the purview of a routineer. The SX-64 has a built-in five inch color monitor 16 and a single disk drive unit 17. The plotter is any one of a number of compatible units, a Commodore VIC 1520 printer/plotter was found to be suitable with the SX-64 and provides a multiple color output.

The microcomputer and plotter referred to are not meant to be restrictive of this inventive concept. They are chosen only to demonstrate the ease at which this concept can be implemented. It is within the choice of one skilled in the art to select others or fabricate a suitable data processing means and still remain within the scope of this concept.

The hand-held keyboard 25 is arranged with two horizontal rows of numeric liquid crystal (or similar) displays 26 and 27. Each row of the horizontal numeric liquid crystal displays shows five digits and beneath each of the five digits in two rows 28 and 29 are aligned, corresponding rows of push-button keys in a one-for-one register. An ON/OFF switch 30 for the unit is included and additional push-button keys 31 and 32 are suitably coupled to give a START/STOP and a BACKSPACE erase capability.

Push-button keyboard 25 was configured to have a frontal area measuring about 6×8 inches to provide a sufficient area for viewing the two horizontal rows of numeric liquid crystal displays 26 and 27 as well as the ten push-buttons on rows 28 and 29. It is to be noted that the horizontal numeric liquid crystal displays and the push-buttons are arranged in a one-for-one register such that a discrete numerical digit is read out by a numeric liquid crystal unit which is immediately above a particular one of the push-button keys. From FIG. 1 it is apparent that the numerical designations are randomized with respect to the push-button keys. Suitable programming provides for such randomization as determined by the testing procedure chosen.

The software for computer display 16 and the randomized digits displayed in rows 26 and 27 is provided for in accordance with accepted techniques that accommodate the capabilities of the Commodore computer and the fabrication of the keyboard. This arrangement is well within the capabilites of one skilled in the art to which this invention pertains and further elaboration at this point is felt to be unnecessary. Let if suffice to say that at the start of a test sequence, after ON/OFF switch 30 has been actuated and START/STOP switch 31 has been depressed the software provides a scrambled numerical sequence 16a on display 16 and a randomly arranged numerical sequence on rows 26 and 27 of push-button keyboard 25. The tested individual copies the scrambled numerical sequences by pushing the appropriate push-button keys in rows 28 and 29 and displays the sequence in row 16b. Errors are erased by pushing BACKSPACE key 32 and pushing the correct push-button. Elapsed time and errors are recorded in the computer on disc drive unit 17.

A suitable records-keeping format is included in the software package to record data on each person tested. Validity of testing is assured by randomizing sequences to be copied and can be provided from a suitable software package. All of this, of course, is done in the assembly language of the Commodore computer or, for that matter, any other equivalent computer system desired.

The Commodore SX-64 was selected for the intended mode of operation because it is a portable microprocessor system that features a built-in 5" color monitor as well as a disc drive that was coupled to a Commodore VIC-1520 printer with its four color, 40-column capability. The detachable keyboard normally provided with the Commodore SX-64 was modified as the keyboard 25 however, to allow changing of the key designations under software control.

The push-button keyboard 25 was designed to have the liquid crystal displays laid out as shown in FIG. 1. The rows of liquid crystal displays 26 and 27 are located on the keyboard with every other digit in the LCDs remaining electrically unconnected in order to provide proper spacing for the push-buttons that are beneath them in rows 28 and 29. The LCDs that are located above the push-buttons are electrically coupled.

Figure 2A:
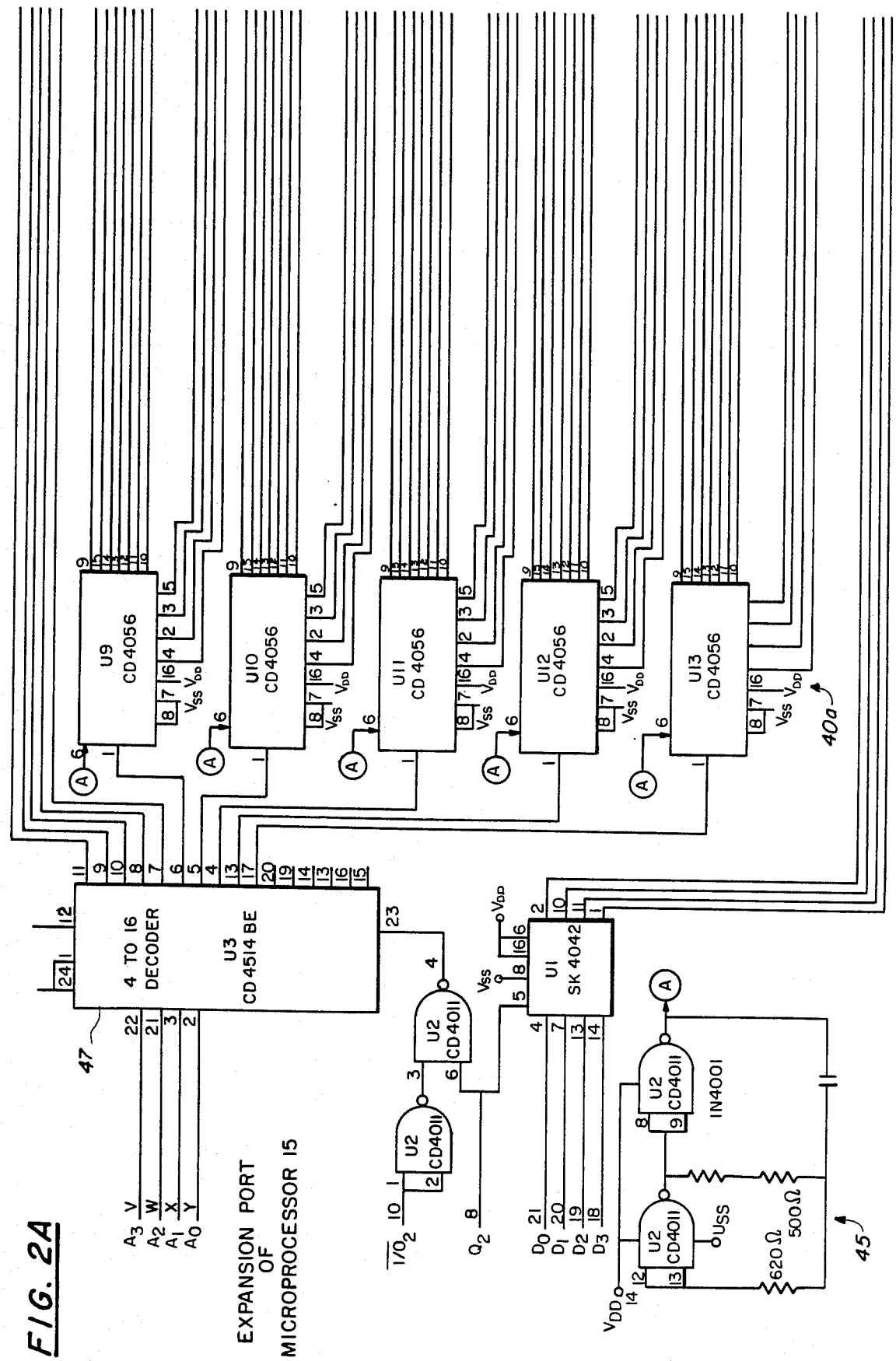
FIGS. 2a and 2b are block diagram representations of some of the electronic elements coupled to the LDCs of the hand-held push-button keyboard.
Figure 2B:
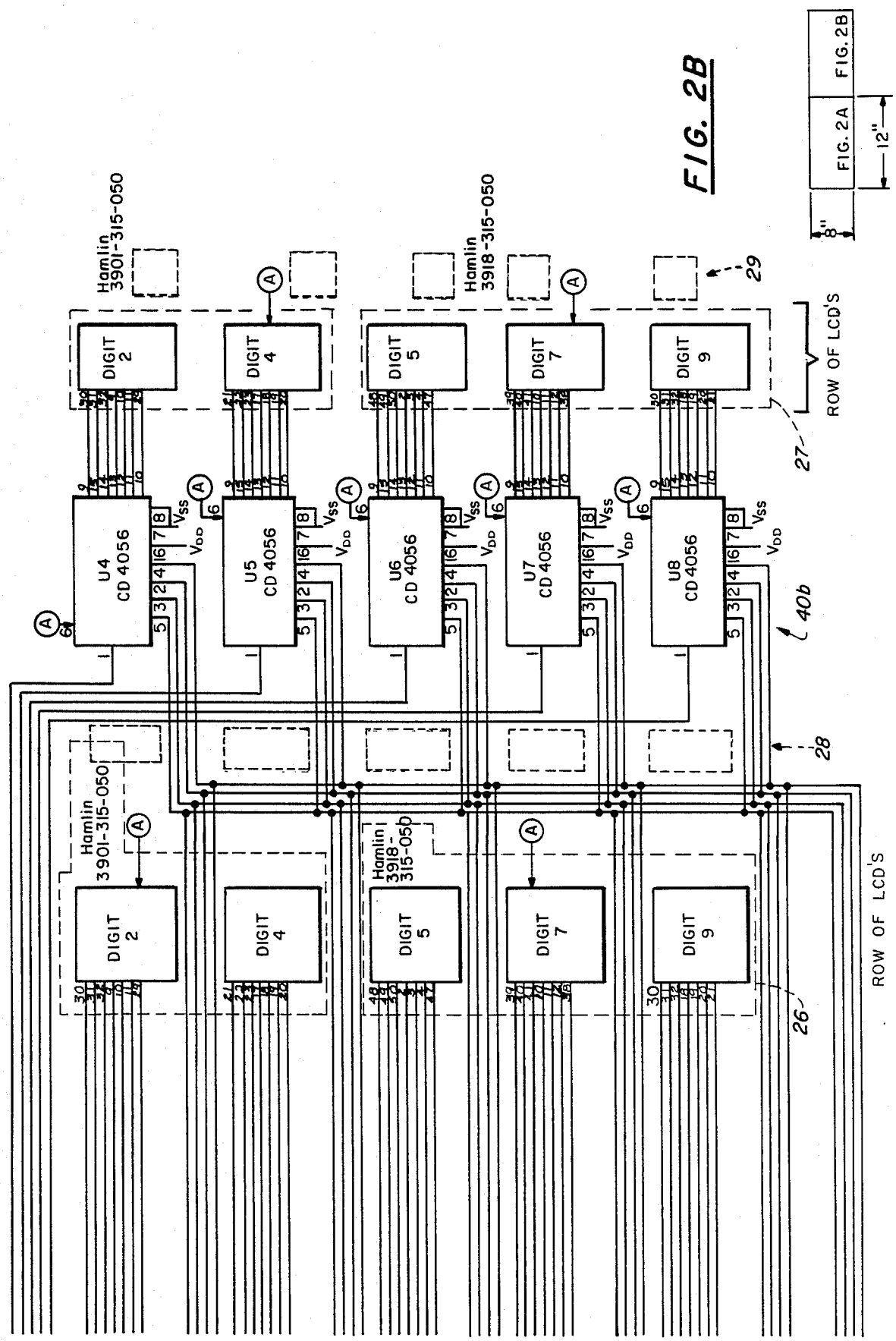

Looking to FIGS. 2a amd 2b, the rows of liquid crystal displays 26 and 27 can be any one of many such units available in the state-of-the-art. Model 3901-315-050s by Hamlin were selected as typical in this embodiment. The liquid crystal display rows were connected to corresponding rows of binary coded decimal-to-seven segment drivers 40a and 40b. Integrated circuit chips RCA-4056s accept the binary data on the Commodore SX-64's expansion port and convert this data into the seven segment information needed by each of the liquid crystal displays. An oscillator 45 having a 50% duty cycle is used to drive the LCDs. Each RCA-4056 chip is addressed by using a decoder 47. The decoder is an RCA-4514 connected to the address bus lines of the microcomputer 16 expansion port and is enabled by an input/output expansion pin of the port. Once enabled, decoder chip 47 decodes the lower four address bits and produces a pulse to match the data from the data bus lines into the appropriate RCA 4056. In this manner a digit is displayed on either lines 26 or 27 on custom keyboard 25.

Figure 3:
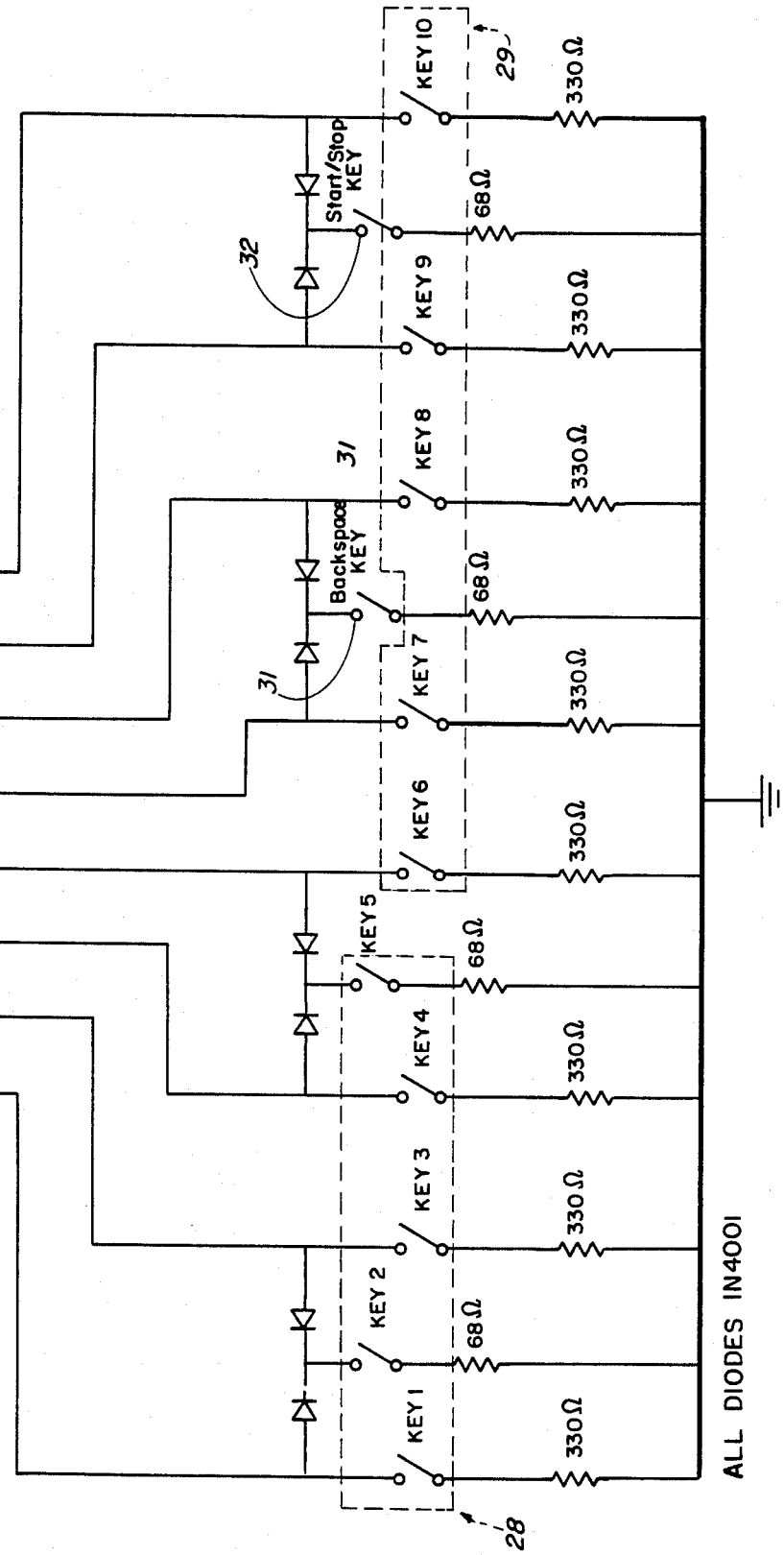
FIG. 3 sets forth schematic details of the elements associated with the push-button keys.

Looking now to FIG. 1 and FIG. 3 the push-buttons in rows 28 and 29 on the keyboard are connected to the user port of the Commodore SX-64. Depressing one of the push-button keys or switches of rows 28 or 29 produces a logical zero at specific pins of the user port on the Commodore SX-64. A connection is made by placing the push button momentary switches in series with pull-down resistors that are connected to ground. Because there are eight pins available on the Commodore SX-64's user port and twelve keys are needed on the special keyboard, appropriately coupled diodes were used to allow some keys to pull down more than one pin simultaneously to allow a unique identification by the microcomputer.

Details of the interconnection of the diodes, all IN4001's, in conjunction with the push-button keys of rows 28 and 29 are noted in the referenced figures. The user port of the Commodore computer as well as the functional interconnection of the push-button keys are shown in FIG. 3. A BACKSPACE key 31 and START/STOP key 32 also are shown coupled by suitable diodes to the user port for responsive operation.

The software which controls the specialized keyboard and runs the reaction time tests was written in assembly language. This language was chosen because of the ease in which programs can wedge into the system interrupt. The system interrupt occurs approximately 120 times a second so that the wedge can be used to scan the keyboard to see if a key is being pressed and to keep track of the different timers that are running. The assembly language wedge is also necessary in order to display up to sixteen sprites (Commodore graphics) simultaneously. Sprites are used so that the enlarged numbers can be read easily on the small 5" monitor.

Figure 4:
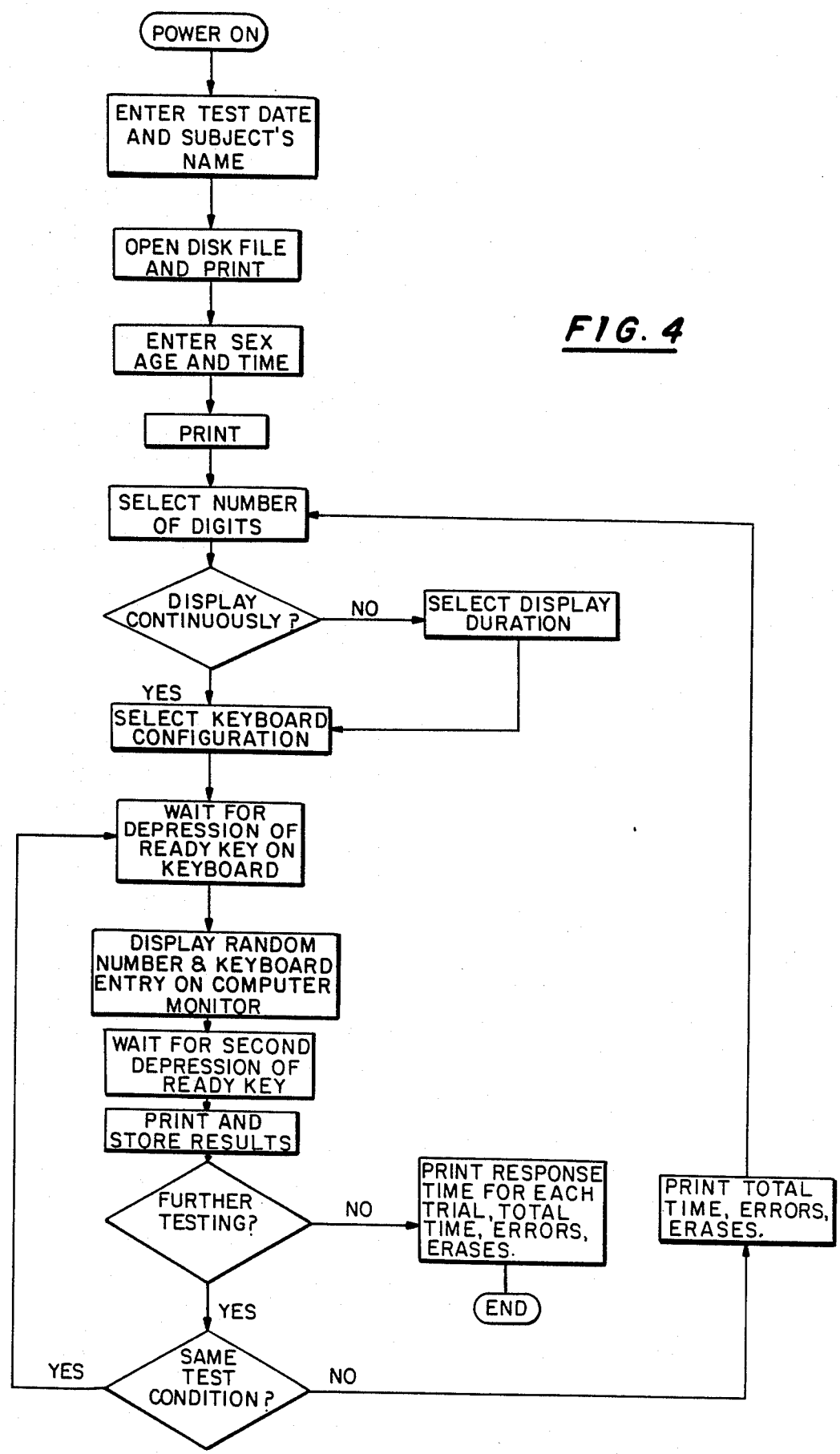
FIG. 4 is a flow diagram of the testing sequence that may be followed with this invention.

With the above disclosed apparatus reaction time data can be gathered. The reaction time to determine whether or not there is a deviation from normal or accepted reaction times probably is most realistically obtained from sampling an individual during known periods of awareness. Large representative samples of general segments of the population might be helpful in some applications; however, a particular individual's history of reaction times provides more meaningful data with respect to that individual during periods of suspected impaired performance. A typical testing procedure of the program is more readily discernible by noting FIG. 4.

Figure 5:
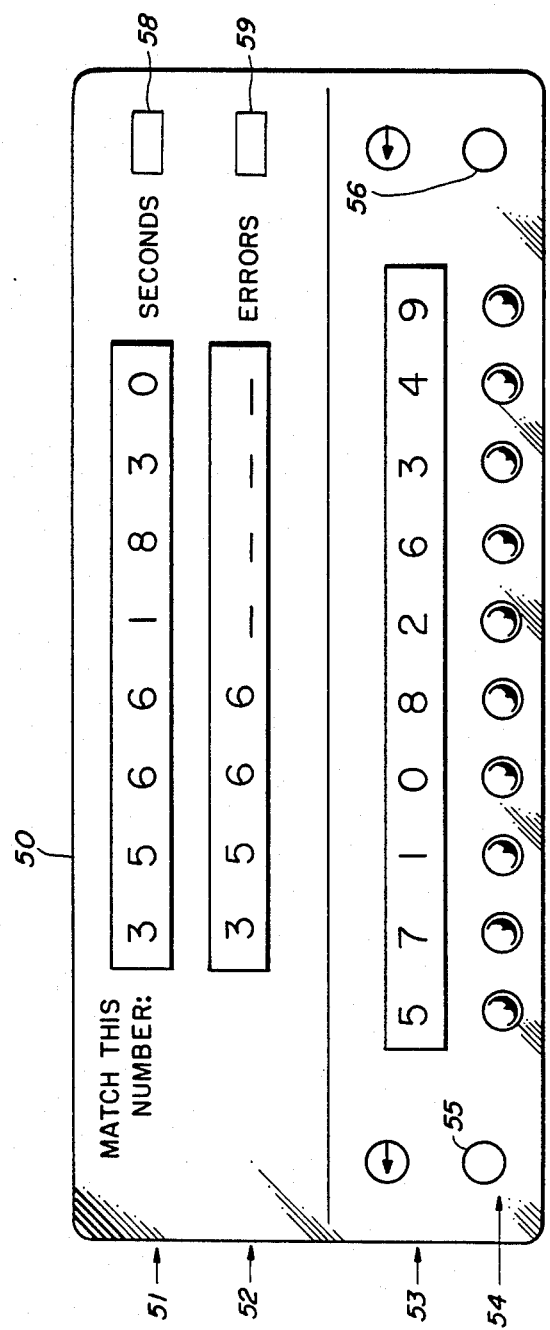
FIG. 5 depicts a variation of the display and push-button key arrangement.

An optional keyboard arrangement is set out in the embodiment of FIG. 5. Here the keyboard 50 has three rows of LCSs 51, 52 and 53 and a single row 54 of push-button key switches. A desired number to match is shown in LCD row 51. The values ascribed to each of the push-buttons in row 54 are in a one-for-one register with the values displayed in LCD row 53. When a START/STOP button 55 is actuated, the number to be matched is shwon in LCDs 51 and the individual under test types on push-buttons 54, the numerical sequence having the values indicated by the LCDs in the one-for-one register aligned numerical designations of row 53. Errors can be visually indicated in LED line 52, and corrections are initiated by first punching BACKSPACE button 56 and repunching the right push-button under the proper number. At the completion of the hoped-to-be-matched number in line 52, the individual under test again pushes the STOP button 55. The time elapsed and the number of errors in the matched number are stored and provide relative indicators of an individual's possible impaired condition. They may be displayed at LCDs 58 and 59.

Erasure of both embodiments can be accomplished at the keyboard by an appropriate switch or at the computer terminal. Since reaction time depends on the chemical activity of the brain and the short term memory of an individual, reaction time under varying conditions can be monitored. These varying reaction times are helpful in recognizing alcohol abuse and/or drug abuse as well as intense fatigue or other nervous disorders. The importance of recognizing all of these symptoms is important due to the demanding and hazardous working conditions in which many are expected to function. Alcohol and drugs are well known to alter the chemical activity of a person's brain and impair recall from short term memory. These effects cause an individual's reaction time to increase and thus decrease the person's performance and ability as tasks are performed.

Testing of an individual can follow several procedures. In one the subject is seated in front of the computer screen with the number entry keyboard in a position where normally one would use a computer keyboard. Parameters are set for the test by an appropriate software package and when the subject is ready, the START/STOP button is depressed. Some permutation of digits appears on the computer's screen and they remain on the screen for the entire trial or vanish after a predetermined duration from, for example, between one-half to five seconds. The LCDs on the face of the display units show digits 0 to 9 in one of twenty possible configurations and remain displayed for the duration of the test.

The goal of the test from the subject's perspective is to note the sequence of the digits appearing on the computer screen and to enter that sequence in the number entry keypad as quickly and accurately as possible. As the subject enters the sequence, it appears on the screen below the original sequence the subject can see the sequence as it is entered and compare it as it corresponds to a one-for-one register with the original. When the entire sequence has been completed, the subject presses the START/STOP button to stop the timer and display the score for that trial. The score shows the time, number of errors and with respect to the embodiment of FIG. 1, the number of erasures and corrections.

The test data of an individual for a number of tests can be compared. Thus, when deviations are noted and it is suspected that an individual's reactions are impaired, further chemical or psychological tests, as the situation calls for, may be initiated or the individual may be relieved from duty until the impaired condition passes.

Several hand-held test units can be coupled to the computer via cables or can include radio transmitters to allow several people to simultaneously take the test which is displayed on a remote large screen display. Optionally, the display and keyboard can have a remote radio link capability. When the appropriate transmission link is included, on-the-job in situ testing of an individual's reaction time can be quickly administered.

A non-portable device enables the testing of one person at a time in, say, a security office at a plant site where each guard might be checked out before he goes on duty. Alternatively, the device can be used at a detention center or police station where a person suspected of being under the influence of alcohol or drugs is tested for impaired reaction. A portable, self-contained unit more suitable for use by security pesonnel on patrol could be used on a work site or at roadside for checking alertness and the level of functioning. This latter also would be particularly useful in testing the alertness of radar or sonar operators, aircraft mechanics, pilots, drivers, etc. for excessive fatigue or drug and alcohol use.

A multi-person aptitude tester such as that referred to above, could be used for testing large groups of subjects at a single time in a common test area. The device could be used to select the most promising persons from a pool of applicants for jobs requiring speed, accuracy and alertness. Each individual keyboard unit would be wired to a central processor which could control the displays and record the results of groups of individuals undergoing tests. Storage of the information and correlation and statistical analysis, etc. can follow after a particular group has been tested under substantially identical conditions and at the same time.

Obviously many modifications and variations of the present invention are possible in the light of the above concepts. It is therefore to be understood that within the scope of the appended claims the invention may be practiced otherwise than as specifically described.

What is claimed is:

1. An apparatus for indicating the mental reaction time of an individual comprising:
   a microcomputer having a suitable program;
   means coupled to the microcomputer for displaying a scrambled sequence of numbers in response to the suitable program;
   means coupled to the microcomputer disposed adjacent the scrambled sequence of numbers displaying means in a one-for-one register thereto for providing a mimicking display thereof;
   means coupled to the microcomputer for displaying a random sequence of numerical designations in response to the suitable program; and
   a plurality of push-button keys each disposed adjacent in a one-for-one register with a particular one of the random sequence of numerical designations coupled to inititate the mimicking display on the providing means in a particular sequence as the push-buttons are punched, the scrambled sequence of numbers displaying means and the random sequence of numerical designation displaying means are juxtaposed arrays of LCDs.

2. A method for testing an individual's reaction time and awareness comprising:

visually displaying a scrambled sequence of numbers on a monitor including the changing thereof to improve the validity of the testing;

visually displaying a random sequence of numerical designations located in a one-for-one register with an array of push-button keys (the random sequence being different than the scrambled sequence);

copying the scrambled sequences of numerical designations by actuating specific ones of the push-button keys that are aligned in a one-for-one register with the random sequence, the process of copying includes the step of backspacing and reactuating the proper push-button key to copy the scrambled sequence when the wrong push-button key was previously incorrectly actuated;

visually monitoring the actually actuated sequence of numbers to note the accuracy of the process of copying; and correlating and timing the results of the time and accuracy of the actually actuated sequence of numbers spent during the step of copying to determine reaction time and awareness, the steps of visually displaying a scrambled sequence of numbers, visually displaying a random sequence of numerical designations and the correlating and timing are under computer control to assure the accuracy thereof and the steps of visually displaying a scrambled sequence, visually displaying a random sequence, copying the scrambled sequence by activating push-buttons and visually monitoring all occur on a hand-held keyboard for individual testing.

* * * * *